United States Patent
Erickson (10) Patent No.: US 10,940,295 B2
(45) Date of Patent: Mar. 9, 2021

(54) MULTI-LUMEN CATHETER DEVICES, SYSTEMS, AND METHODS OF USING THE SAME

(71) Applicant: Kurt W. Erickson, Chicago, IL (US)

(72) Inventor: Kurt W. Erickson, Chicago, IL (US)

(*) Notice: Subject to any disclaimer, the term of this patent is extended or adjusted under 35 U.S.C. 154(b) by 175 days.

(21) Appl. No.: 15/375,923

(22) Filed: Dec. 12, 2016

(65) Prior Publication Data

US 2017/0259033 A1 Sep. 14, 2017

Related U.S. Application Data

(60) Provisional application No. 62/241,058, filed on Oct. 13, 2015.

(51) Int. Cl.
| | | |
|---|---|---|
| *A61M 25/10* | (2013.01) | |
| *A61F 2/958* | (2013.01) | |
| *A61F 2/954* | (2013.01) | |
| *A61M 25/00* | (2006.01) | |

(52) U.S. Cl.
CPC ........... *A61M 25/104* (2013.01); *A61F 2/954* (2013.01); *A61F 2/958* (2013.01); *A61M 25/003* (2013.01); *A61M 2025/1045* (2013.01)

(58) Field of Classification Search
CPC .............. A61M 25/104; A61M 25/003; A61M 2025/1045; A61F 2/954; A61F 2/958
See application file for complete search history.

(56) References Cited

U.S. PATENT DOCUMENTS

| | | |
|---|---|---|
| 4,183,102 A | 1/1980 | Guiset |
| 4,909,252 A | 3/1990 | Goldberger |
| 5,108,370 A | 4/1992 | Walinsky |
| 5,433,706 A | 7/1995 | Abiuso |
| 5,470,314 A | 11/1995 | Walinsky |
| 5,613,980 A * | 3/1997 | Chauhan ........... A61M 25/1002 128/898 |
| 6,099,497 A | 8/2000 | Adams |
| 6,709,440 B2 | 3/2004 | Callol |
| 6,808,510 B1 * | 10/2004 | DiFiore ............... A61M 1/3653 604/171 |
| 7,591,846 B2 | 9/2009 | Vardi |
| 2004/0167463 A1 * | 8/2004 | Zawacki ............. A61M 1/3659 604/43 |
| 2006/0149350 A1 * | 7/2006 | Patel ....................... A61F 2/954 623/1.11 |
| 2011/0245665 A1 * | 10/2011 | Nentwick ......... A61M 25/0029 600/433 |

* cited by examiner

*Primary Examiner* — Tan-Uyen T Ho
*Assistant Examiner* — Chima U Igboko
(74) *Attorney, Agent, or Firm* — Nixon Peabody LLP (57) ABSTRACT

A dual guidewire lumen catheter includes a first elongated member and a second elongated member. The first elongated member includes a first integral portion, a first free portion, and a first lumen extending there through. The first lumen is configured to receive a first guidewire. The first free portion has a first distal end and a first aperture configured to receive the first guidewire. The second elongated member includes a second distal end and a second lumen there through. The second lumen is configured to receive a second guidewire and the second distal end has a second aperture configured to receive the second guidewire. The second elongated member is integral with the first integral portion of the first elongated member and the first free portion is moveable with respect to a central axis of the catheter.

6 Claims, 10 Drawing Sheets

MULTI-LUMEN CATHETER DEVICES, SYSTEMS, AND METHODS OF USING THE SAME

CROSS-REFERENCE TO RELATED APPLICATIONS

This application claims the benefit and priority to U.S. Provisional Application No. 62/241,058, filed on Oct. 13, 2015, which is hereby incorporated by reference herein in its entirety.

TECHNICAL FIELD

The present disclosure relates generally to catheters and, more particularly, to catheters used at a bifurcation of a vessel.

BACKGROUND

Percutaneous revascularization of narrowed or occluded vessels (e.g., arteries) is standard in the practice of cardiovascular medicine. Often, lesions located at a vessel bifurcation (or simply bifurcation) are difficult to open percutaneously. Dilation or stent placement within a parent vessel or a main branch of the bifurcation can shift plaque into one or more side branches of the bifurcation, resulting in ischemia or infarction of the myocardium supplied by the one or more side branches. Once plaque is shifted into a side branch of the bifurcation, access to the side branch may be difficult or impossible, further placing the patient at risk for ischemia or myocardial infarction. Thus, new devices, systems, and methods are needed to provide access (e.g., continuous access) to both branches of a bifurcation during treatment of a lesion occurring at the bifurcation. The present disclosure addresses these and other problems.

SUMMARY

According to some aspects of the present disclosure, a multi-lumen catheter includes a first elongated member and a second elongated member. The first elongated member includes an integral portion, a first free portion, and a first lumen extending there through. The first lumen is configured to receive a first guidewire and the first free portion has a first distal end and a first aperture configured to receive the first guidewire. The second elongated member includes a second distal end and a second lumen extending there through. The second lumen is configured to receive a second guidewire and the second distal end has a second aperture configured to receive the second guidewire. The second elongated member is integral with the integral portion of the first elongated member and the first free portion is moveable with respect to a central axis of the catheter.

According to some aspects of the present disclosure, a dual guidewire lumen catheter system includes a catheter and a balloon. The catheter includes a first elongated member and a second elongated member. The first elongated member includes a first integral portion, a first free portion, and a first lumen extending there through. The first lumen is configured to receive a first guidewire. The first free portion of the first elongated member has a first distal end and a first aperture configured to receive the first guidewire. The second elongated member includes a second distal end and a second lumen extending there through. The second lumen is configured to receive a second guidewire. The second distal end of the second elongated member has a second aperture configured to receive the second guidewire. The second elongated member is integral with the first integral portion of the first elongated member and the first free portion is moveable with respect to a central axis of the catheter. The balloon is coupled to the catheter and is configured to dilate a vessel and/or deploy a stent at a bifurcation of a vessel.

According to some aspects of the present disclosure, a method includes providing a catheter having a first elongated member and a second elongated member at a vessel bifurcation. The first elongated member includes a first free portion, a first integral portion, and a first lumen extending there through. The first free portion has a first aperture. The second elongated member includes a second integral portion, a second free portion, and a second lumen extending there through. The second integral portion is integral with the first integral portion of the first elongated member and the second free portion is spaced from the first free portion and having a second aperture. A balloon is provided and is coupled to the catheter. A first guidewire is advanced through the first lumen of the first elongated member of the catheter and the first aperture of the first free portion into a parent vessel of the vessel bifurcation and into a side branch of the vessel bifurcation. A second guidewire is advanced through the second lumen of the second elongated member of the catheter and the second aperture of the second free portion into the parent vessel of the vessel bifurcation. The catheter is advanced along the first guidewire and the second guidewire into the parent vessel. The second guidewire is advanced into a main branch of the bifurcation. The catheter is advanced along the first guidewire and the second guidewire to the bifurcation of the parent vessel.

These and other aspects of the present disclosure will become more apparent from the following detailed description of the devices, systems, and methods in conjunction with the accompanying drawings.

The present disclosure is susceptible to various modifications and alternative forms, and some representative aspects have been shown by way of example in the drawings and will be described in detail herein. It should be understood, however, that the inventive aspects of the disclosure are not limited to the particular forms disclosed. Rather, the disclosure is to cover all modifications, equivalents, and alternatives falling within the spirit and scope of the invention as defined by the appended claims.

DETAILED DESCRIPTION

The present disclosure concerns a multi-lumen guidewire catheter device and system that are configured to be deployed in a blood vessel at a bifurcation of the blood vessel. Although described and illustrated primarily as a dual guidewire lumen catheter herein, the catheter can have any number of lumens, for example, three lumens, four lumens, six lumens, ten lumens, etc. Advantageously, providing multiple lumens allows separate guidewires to be advanced through each lumen without the guidewires becoming intertwined. Moreover, in some aspects, the multi-lumen catheter includes a number of elongated members, and each elongated member can have a free portion. Each of free portions is moveable with respect to a central axis of the catheter such that each free portion can be positioned at or near a branch of the bifurcation.

Referring generally to FIGS. 1A-1D, a dual guidewire lumen catheter 100 includes a first elongated member 102a and a second elongated member 102b. In some aspects of the present disclosure, the dual guidewire lumen catheter 100 is configured to be deployed in a parent vessel having a bifurcation. Beyond the bifurcation, the parent vessel branches off into, for example, a side branch and a main branch. However, in some aspects, the parent vessel can branch off into more than two branches.

Figure 1A:
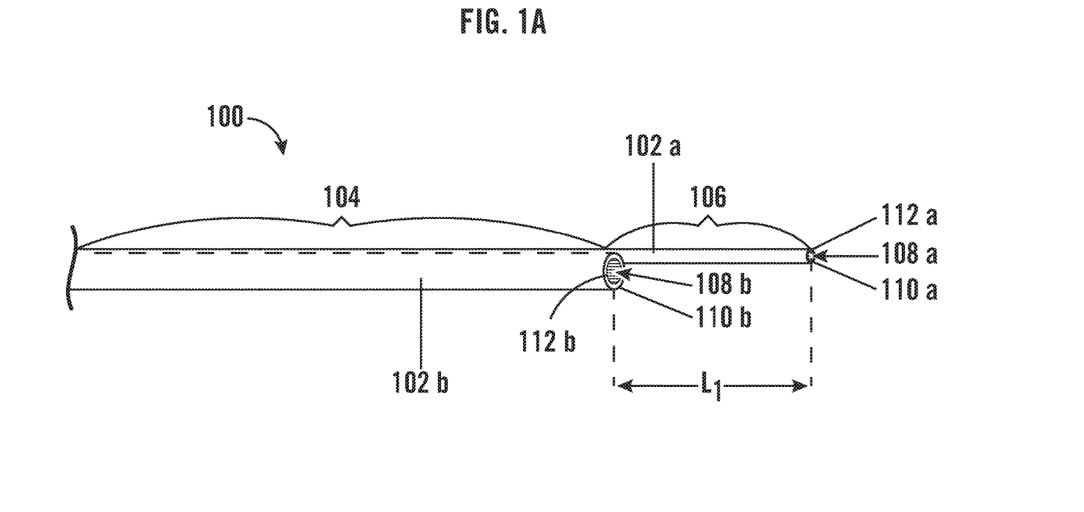
FIG. 1A is a perspective view of a portion of a dual guidewire lumen catheter according to some aspects of the present disclosure.
Figure 1B:
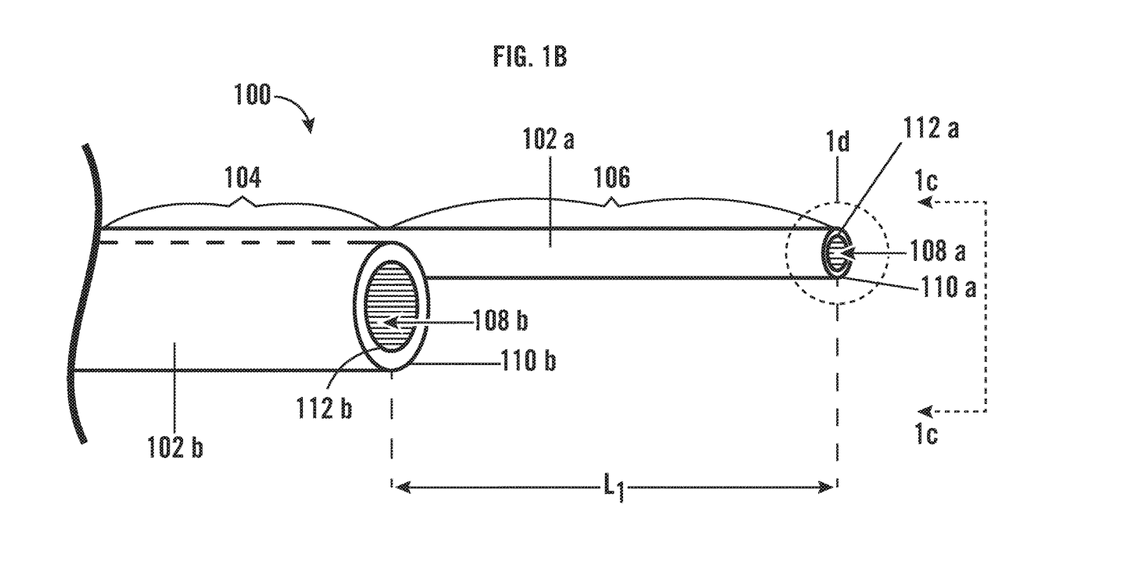
FIG. 1B is a detailed perspective view of an end of the dual guidewire lumen catheter of FIG. 1A according to some aspects of the present disclosure.

Referring to FIGS. 1A and 1B, the first elongated member 102a of the dual guidewire lumen catheter 100 includes an integral portion 104, a free portion 106, and a first lumen 108a extending there through. The free portion 106 includes a first distal end 110a having a first distal aperture 112a. The first lumen 108a is configured to receive a first guidewire (not shown) such that the first guidewire can be advanced through a first proximal end (not shown) of the first elongated member 102a and extend through the first distal aperture 112a of the first distal end 110a. Thus, the diameter of the first lumen 108a is greater than the diameter of the first guidewire in order to facilitate movement of the first guidewire within the first lumen 108a. As shown, the first lumen 108a has a generally cylindrical configuration (e.g., cross-section). Alternatively, the first lumen 108a can have any other configuration, such as, for example, a rectangular cross-section, a triangular cross-section, an oval cross-section, a semi-circular cross-section, and/or any polygonal cross-section. In some aspects, the configuration of the first lumen 108a is circular to correspond to a circular configuration of a balloon or a stent that is deployed by the first elongated member 102a.

The second elongated member 102b of the dual guidewire lumen catheter 100 includes a second lumen 108b and a second distal end 110b having a second distal aperture 112b. The second lumen 108b is configured to receive a second guidewire (not shown) such that the second guidewire can be advanced through a second proximal end (not shown) of the second elongated member 102b and extend through the second distal aperture 112b of the second distal end 110b. Similar to above, the diameter of the second lumen 108b is greater than the diameter of the second guidewire in order to facilitate movement of the second guidewire within the second lumen 108b. As shown, the second lumen 108b has a generally cylindrical configuration. The configuration of the second lumen 108b can be the same as or similar to the configuration of the first lumen 108a. Alternatively, the second lumen 108b can have any other suitable configuration as described above with respect to the first lumen 108a.

As depicted, the first elongated member 102a and the second elongated member 102b each have a generally cylindrical configuration (e.g., cross-section). Alternatively, the first elongated member 102a and/or the second elongated member 102b can have any other configuration, such as, for example, a rectangular cross-section, a triangular cross-section, an oval cross-section, a semi-circular cross-section, and/or any polygonal cross-section. Moreover, as shown, the first elongated member 102a and first lumen 108a have the same or similar configuration. Alternatively, the first elongated member 102a and the first lumen 108a can have different configurations, such as, for example, an oval configuration and a generally cylindrical configuration respectively. Likewise, the second elongated member 102b and the second lumen 108b can have the same, similar, or different configurations.

The first elongated member 102a and the second elongated member 102b can be made of the same material and/or a combination of different materials. For example, the first elongated member 102a and the second elongated member 102b can be made of a medical-grade silicone polymer material.

Figure 1C:
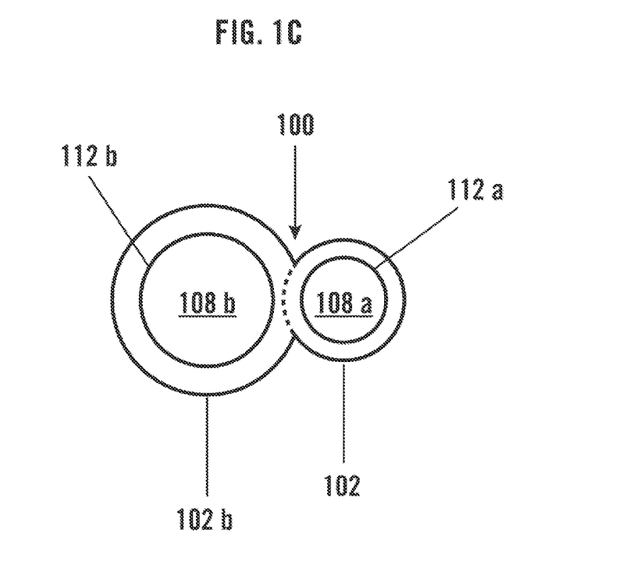
FIG. 1C is an end-on view of the dual guidewire lumen catheter of FIG. 1A according to some aspects of the present disclosure.

In some aspects, the second elongated member 102b is directly attached to the integral portion 104 of the first elongated member 102a. As best shown in FIG. 1C, the integral portion 104 of the first elongated member 102a is directly attached to the second elongated member 102b such that the integral portion 104 and second elongated member 102b are unitary and/or monolithic. However, in some aspects, the integral portion 104 and the second elongated member 102b can be separate and distinct elements that are attached via a welded connection, an adhesive or glue connection, a locking collar, a pin and aperture system, tabs, or the like, or any combination thereof. Advantageously, a unitary and/or monolithic configuration aids in preventing the integral portion 104 from separating from the second elongated member 102b while the dual guidewire lumen catheter 100 is deployed in a vessel.

In such aspects where the integral portion 104 and second elongated member 102b are separate and distinct elements, the second elongated member 102b can have a curved or generally "U" shaped channel that corresponds to the diameter of the integral portion 104. In this configuration, the curved or "U" shaped channel receives the integral portion 104. The second elongated member 102b and the integral portion 104 are then attached using one of the methods described above. Alternatively, the integral portion 104 can have a curved or "U" shaped configured to receive the second elongated member 102b.

Alternatively still, the integral portion 104 can be attached to the second elongated member 102b via an intermediate central portion. In such aspects, the integral portion 104 is attached to the intermediate central portion and the second elongated member 102b is also attached to an opposing side of the intermediate central portion using one of the methods described above. In this configuration, the distance between the first lumen 108a of the first elongated member 102a and the second lumen 108b of the second elongated member 102b corresponds to the thickness of the intermediate central portion.

As shown in FIGS. 1A and 1B, the free portion 106 of the first elongated member 102a can extend beyond the second elongated member 102b by a length L1, which can be about one to ten millimeters. The length L1 of the free portion 106 can vary depending on the geometry of the bifurcation of the vessel in which it is to be deployed. For example, the dual guidewire catheter 100 can be deployed in a parent vessel having a bifurcation branching off into a main branch and a side branch. The length L1 of the free portion 106 can correspond to the required length for the distal end 110a of the free portion 106 to substantially reach into, for example, the side branch, such as to access a lesion within the side branch. Further, the free portion 106 is moveable with respect to the second elongated member 102b. As such, for example, the free portion 106 can be positioned at or near the side branch of the bifurcation while the second elongated member 102b is simultaneously positioned at or near the main branch. This configuration thus aids in allowing the dual guidewire lumen catheter 100 to be used in a variety of bifurcation geometries.

As best shown in FIG. 1C, in some aspects, the second elongated member 102b has a diameter that is greater than a diameter of the first elongated member 102a. However, other configurations are contemplated, such as, for example, the first elongated member 102a having a diameter substantially equal to the diameter of the second elongated member 102b, or the first elongated member 102a having a diameter that is greater than the diameter of the second elongated member 102b. In addition, the respective diameters of the first elongated member 102a and the second elongated member 102b can depend upon the diameter of the parent vessel, the corresponding main branch, the corresponding side branch, and/or the diameter of the first and second lumens.

Providing a first lumen 108a and a second lumen 108b allows for parallel placement of the first guidewire and the second guidewire, eliminating the risk of the guidewires becoming intertwined. For example, the first guidewire can be advanced through the first lumen 108a of the first elongated member 102a to a side branch, and the second guidewire can be advanced through the second lumen 108b of the second elongated member 102b to a main branch. In this configuration, the dual guidewire lumen catheter 100 prevents the first guidewire from interacting with the second guidewire through the dual guidewire lumen catheter 100. By eliminating the risk of the guidewires becoming intertwined, the dual guidewire lumen catheter 100 aids in placement of subsequent devices (e.g., subsequent catheters, balloon, stents, etc.), which otherwise could be hindered by crossed guidewires.

Figure 1D:
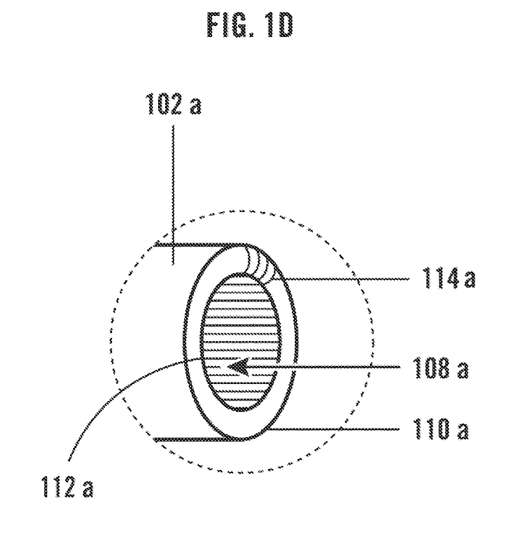
FIG. 1D is a close-up perspective view of the dual guidewire lumen catheter of FIG. 1A according to some aspects of the present disclosure.
Figure 1E:
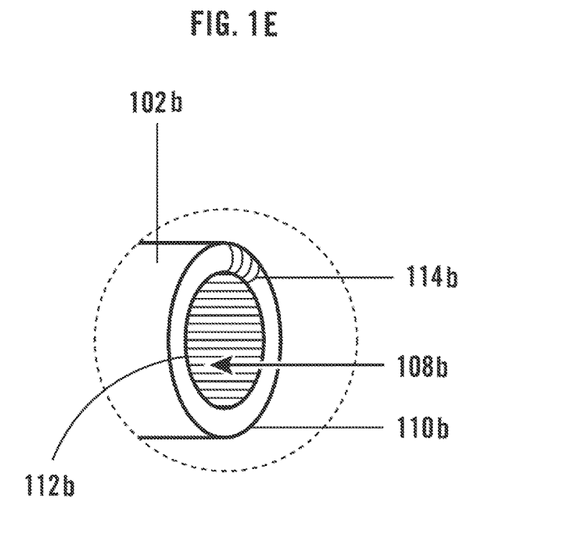
FIG. 1E is a close-up perspective view of the dual guidewire lumen catheter of FIG. 1A according to some aspects of the present disclosure.

As best shown in FIGS. 1D and 1E, in some aspects, the first distal end 110a of the free portion 106 has a first beveled surface 114a. The first beveled surface 114a is configured to aid in placement of the first guidewire (not shown) within the main branch or the side branch of the bifurcation. Additionally, the first beveled surface 114a reduces or eliminates sharp edges at the distal end 110a of the free portion 106, thereby eliminating the risk of injury to the vessel or side branches. The second distal end 110b can also have a second beveled surface 114b to aid in placement of the second guidewire within the main branch or the side branch of the bifurcation. The second beveled surface 114b can be the same as or similar to the first beveled surface 114a. Alternatively, the second beveled surface 114b can be beveled at a different curvature than the first beveled surface 114a to facilitate placement of the second guidewire at a different angle than the first guidewire. The first beveled surface 114a and/or the second beveled surface 114b can be made of the same or different materials or combination of materials than the first elongated member 102a and/or the second elongated member 102b.

Figure 2:
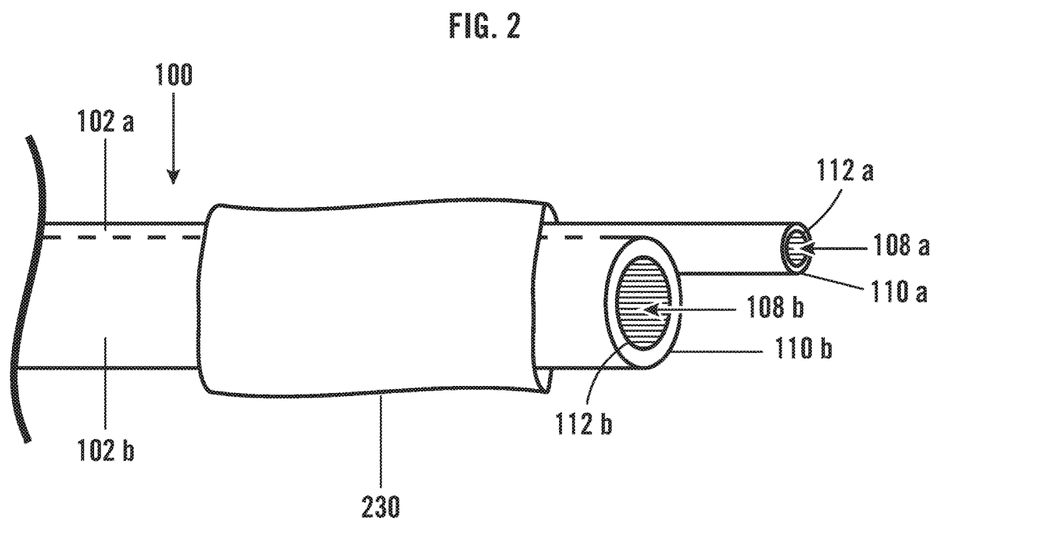
FIG. 2 is a perspective view of the dual guidewire lumen catheter of FIG. 1A with a balloon coupled thereto according to some aspects of the present disclosure.

As depicted in FIG. 2, in some aspects, the dual guidewire lumen catheter 100 includes a balloon 230 coupled thereto. The balloon 230 is configured to expand to the contours of a vessel and/or expand or dilate the vessel, such as the parent vessel. As shown, the balloon 230 is coupled to the dual guidewire lumen catheter 100 such that the first distal end 110a and second distal end 110b extend beyond the balloon 230. The extent to which the first distal end 110a and second distal end 110b extend beyond the balloon 230 depends on the geometry of the target bifurcation. For example, the first distal end 110a may need to extend further beyond the balloon 230 than the second distal end 110b to permit the first distal end 110a to be positioned at or near a side branch of the bifurcation. Further, the balloon 230 is sized and shaped such that the first elongated member 102a and the second elongated member 102b are disposed within an opening of the balloon 230.

Figure 3:
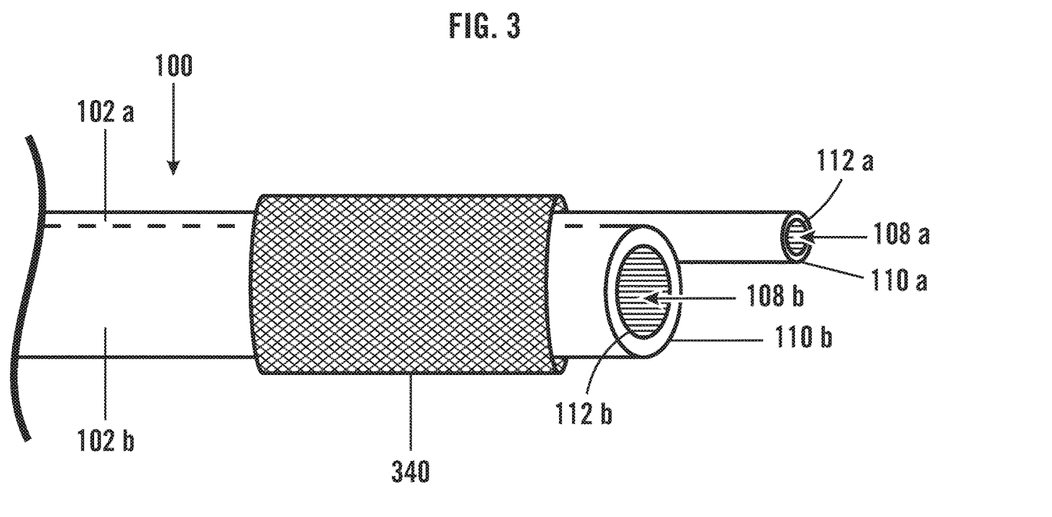
FIG. 3 is a perspective view of the dual guidewire lumen catheter and balloon of FIG. 2 with a stent arranged over the balloon according to some aspects of the present disclosure.

Referring to FIG. 3, in some aspects, the dual guidewire lumen catheter 100 includes a stent 340. In such aspects, the stent 340 is coupled to the balloon 230 (not shown) such that dilation of the balloon 230 causes the stent 340 to be deployed. The stent 340 is appropriately sized such that it can be deployed within the target vessel. Deployment of the stent 340 can be optimized, if necessary, with existing intravascular imaging techniques.

In some aspects of the present disclosure, the dual guidewire lumen catheter 100 is a balloon and stent design with a central perfusion balloon. Advantageously, the central perfusion balloon can define a channel or aperture when it is inflated to allow blood to flow past the balloon while inflated. Any of the balloons subsequently described herein with respect to some aspects of the present disclosure can be a central perfusion balloon.

Advantageously, the dual guidewire lumen catheter 100 provides continuous access to both branches of a bifurcation when deploying the stent in a bifurcated parent vessel. Advancing the first guidewire through the first elongated member 102a into a branch of the bifurcation and the second guidewire through the second elongated member 102b into another branch of the bifurcation prevents the dual guidewire lumen catheter 100 from being inadvertently advanced into either branch. As described above, the geometry and dimensions of the dual guidewire lumen catheter 100 can be modified to correspond to the geometry of any bifurcation. Further, this configuration aids in preventing plaque shift from the parent vessel or a main branch to a side branch, thereby reducing the risk of complications for a patient and increasing the success rate of treating a lesion occurring a bifurcation.

Figure 4A:
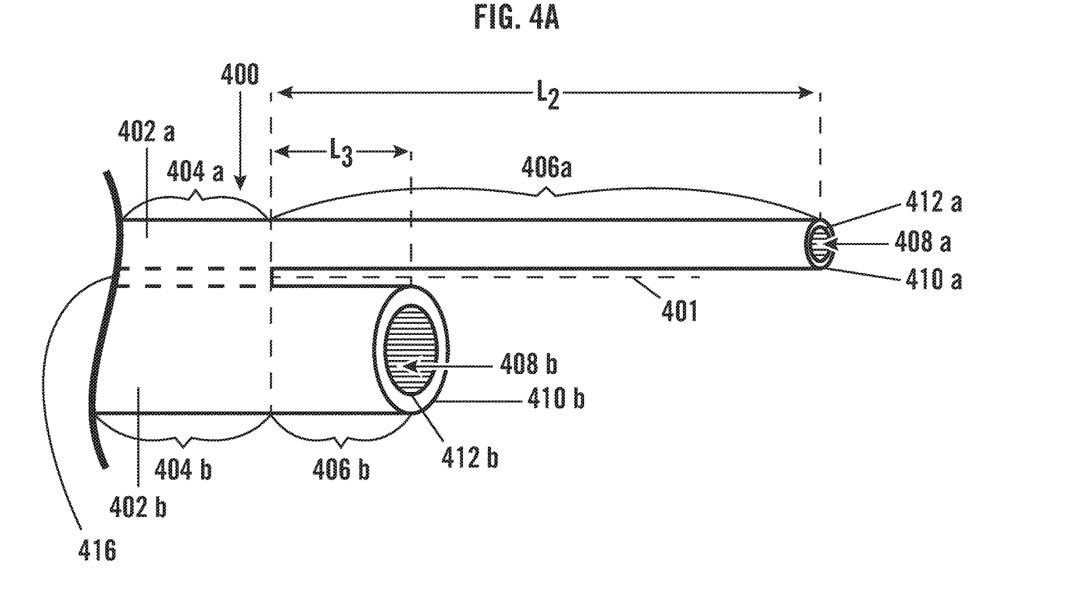
FIG. 4A is a perspective view of a portion of a dual guidewire lumen catheter according to some aspects of the present disclosure.
Figure 4B:
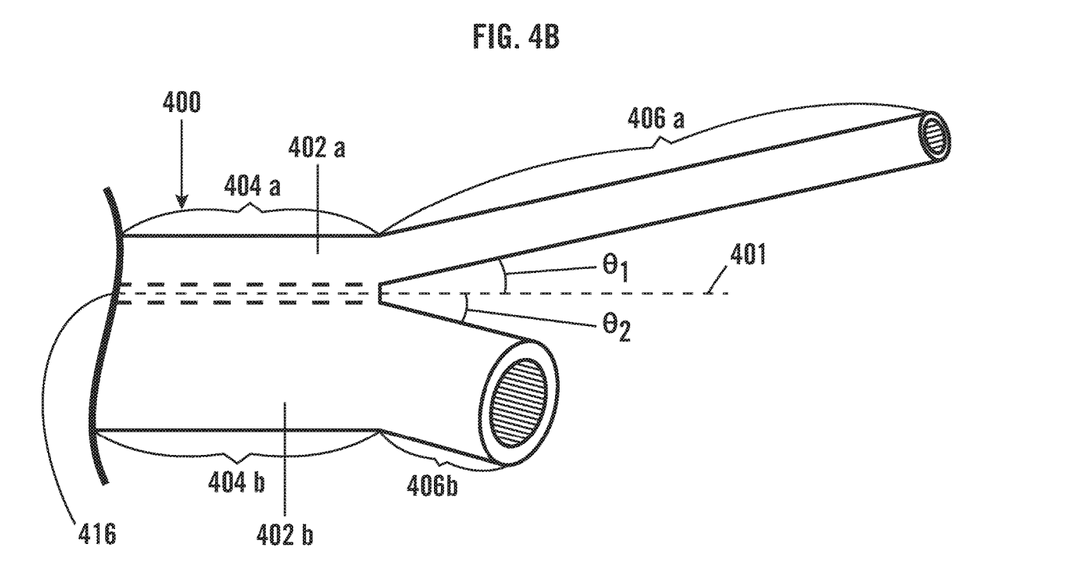
FIG. 4B is another perspective view of the dual guidewire lumen catheter of FIG. 4A according to some aspects of the present disclosure.
Figure 4C:
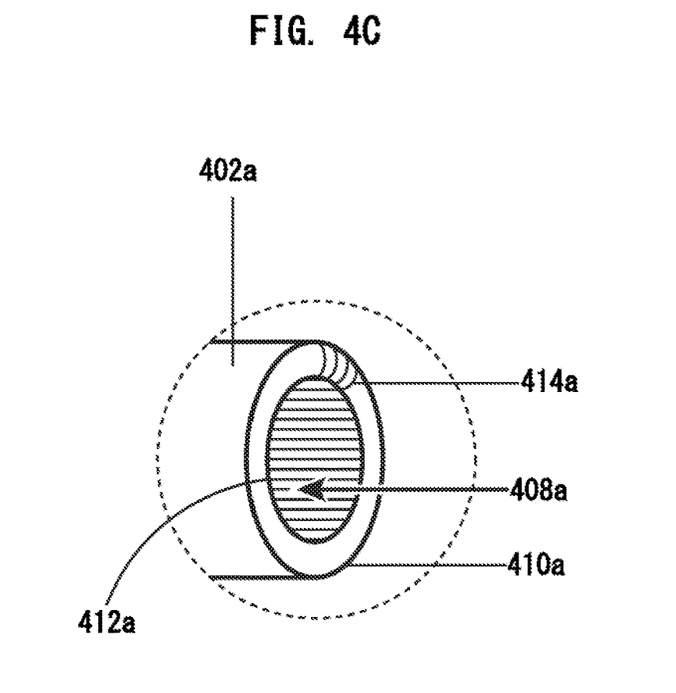
FIG. 4C is a close-up perspective view of the first free portion of the dual guidewire lumen catheter of FIG. 4A according to some aspects of the present disclosure.
Figure 4D:
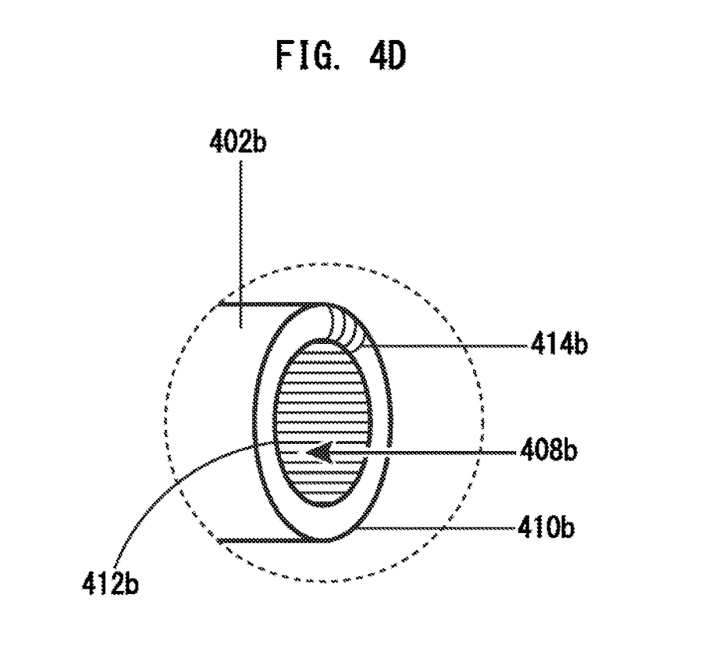
FIG. 4D is a close-up perspective view of the second free portion of the dual guidewire lumen catheter of FIG. 4A according to some aspects of the present disclosure.

Referring to FIGS. 4A and 4B, a dual guidewire lumen catheter 400 is shown. The dual guidewire lumen catheter 400 is similar to the dual guidewire lumen catheter 100 shown in FIGS. 1A-1D in that the dual guidewire lumen catheter 400 includes a first elongated member 402a and a second elongated member 402b. The dual guidewire lumen catheter 400 is configured to be deployed in a blood vessel having a bifurcation.

The first elongated member 402a of the dual guidewire lumen catheter 400 includes a first integral portion 404a, a first free portion 406a, and a first lumen 408a extending there through. The first free portion 406a includes a first distal end 410a having a first distal aperture 412a. The first lumen 408a is configured to receive a first guidewire (not shown) such that the first guidewire can be advanced through the first elongated member 402a and the first distal aperture 412a of the first distal end 410a. The diameter of the first lumen 408a generally corresponds to the diameter of the first guidewire. Thus, the diameter of the first lumen 408a is greater than the diameter of the first guidewire in order to facilitate movement of the first guidewire within the first lumen 408a. Thus, generally, the first elongated member 402a of the dual guidewire lumen catheter 400 is substantially similar to the first elongated member 102a of the dual guidewire lumen catheter 100 (FIGS. 1A-1D).

The second elongated member 402b of the dual guidewire lumen catheter 400 differs from the second elongated member 102b of the dual guidewire lumen catheter 100 (FIGS. 1A-1D) in that the second elongated member 402b includes a second free portion 406b, in addition to a second integral portion 404b, and a second lumen 408b extending there through. The second free portion 406b includes a second distal end 410b having a second distal aperture 412b. The second lumen 408b is configured to receive a second guidewire (not shown) such that the second guidewire can be advanced through the second elongated member 402b and the second distal aperture 412b of the second distal end 410b. The diameter of the second lumen 408b generally corresponds to the diameter of the second guidewire. Thus, the diameter of the second lumen 408b is greater than the diameter of the second guidewire in order to facilitate movement of the second guidewire within the second lumen 408b.

As depicted, the first elongated member 402a and the second elongated member 402b have a generally cylindrical configuration. Alternatively, the first elongated member 402a and the second elongated member 402b can have any other configuration, such as, for example, a rectangular configuration, a triangular configuration, an oval configuration, a semi-circular configuration, and/or polygonal configuration. Moreover, as shown, the first elongated member 402a and first lumen 408a have the same or similar generally cylindrical configuration. Alternatively, the first elongated member 402a and the first lumen 408a can have different configurations, such as, for example, an oval configuration and a generally cylindrical configuration respectively. Likewise, the second elongated member 402b and the second lumen 108b can have the same or different configurations.

The first elongated member 402a and the second elongated member 402b can be made of the same and/or a combination of different materials. For example, the first elongated member 402a and the second elongated member 402b can be made of a medical-grade polymer material.

As depicted, the first integral portion 404a of the first elongated member 402a is directly attached to a central portion 416. Likewise, the second integral portion 404b is directly attached to an opposing side of the central portion 416. As shown, the first integral portion 404a, the central portion 416, and the second integral portion 404b are unitary and/or monolithic elements. However, the first integral portion 404a, the central portion 416, and the second integral portion 404b can be separate and distinct elements that can be attached via a welded connection, an adhesive or glue connection, a locking collar, a pin and aperture system, tabs, or the like, or any combination thereof. The first integral portion 404a, the central portion 416, and the second integral portion 404b can be made of the same material and/or a combination of different materials. Advantageously, a unitary and/or monolithic configuration aids in preventing the first integral portion 404a and/or the second integral portion 404b from separating from the central portion 416 while the dual guidewire lumen catheter 400 is deployed in a vessel.

Alternatively, in some aspects, the first elongated member 402a and second elongated member 402b can be directly attached to one another. In this configuration, like the elongated members 102a, 102b of the dual guidewire lumen catheter 100 of FIGS. 1A-1D, the first elongated member 402a and the second elongated member 402b can be unitary and/or monolithic. Alternatively, the elongated members 402a, 402b can be separate and distinct elements that can be attached via a welded connection, an adhesive or glue connection, a locking collar, a pin and aperture system, tabs, or the like, or any combination thereof.

In such aspects where the first integral portion 404a, the central portion 416, and the second integral portion 404b are separate and distinct elements, the central portion 416 can have a first curved or generally "U" shaped channel that corresponds to the diameter of the first integral portion 404a and a second curved or generally "U" shaped channel that corresponds to the diameter of the second integral portion 404b. In this configuration, an outer surface of the first integral portion 404a is directly attached to the first channel of the central portion 416 and an outer surface of the second integral portion 404b is directly attached to the second channel of the central portion 416.

As shown in FIG. 4A, the first free portion 406a extends beyond the first integral portion 404a of the first elongated member 402a by a length L2, which can be about one to ten millimeters. The length L2 can correspond to the geometry of a branch of the bifurcation. For example, if the first free portion 406a corresponds to a side branch, the length L2 can correspond to an appropriate dimension of the side branch. Similarly, the second free portion 406b extends beyond the second integral portion 404b of the second elongated member 402b by a length L3, which can be about one to ten millimeters. The length L3 of the second free portion 406b can correspond to the geometry of another branch of the bifurcation. For example, if the second free portion 406b corresponds to a main branch of the bifurcation, the length L3 can correspond to an appropriate dimension of the main branch.

As shown in FIG. 4A, the length L2 of the first free portion 406a is greater than the length L3 of the second free portion 406b. Alternatively, depending on the geometry of the target bifurcation, the length L2 and the length L3 can be substantially the same, or the length L3 can be greater than the length L2. By permitting variable sizing of the length L2 and the length L3, the dual guidewire lumen catheter 400 can be configured for use with a bifurcation having any given dimensions or geometries.

Attaching the first integral portion 404a, the central portion 416, and the second integral portion 404b such that the first free portion 406a is spaced from the second free portion 406b facilitates movement of the first free portion 406a and second free portion 406b with respect to a central axis 401. The extent to which the first free portion 406a is spaced from the second free portion 406b corresponds to the thickness of the central portion 416. As depicted in FIG. 4B, the first free portion 406a is moveable with respect to the central axis 401 by an angle $\theta_1$. The values of the angle $\theta_1$ can be, for example, ten degrees, forty-five degrees, ninety degrees, one-hundred thirty-five degrees, one-hundred eighty degrees, etc. Desirably, the angle $\theta_1$ corresponds to the geometry of a side branch of a bifurcation in a parent vessel. For example, the angle $\theta_1$ can be substantially equal to an angle at which a side branch extends from a central axis of the bifurcation of the parent vessel. By allowing the value for the angle $\theta_1$ to range between at least zero degrees and one-hundred eighty degrees, the first free portion 406a can be positioned at or near a branch of a bifurcation having any given geometry.

Likewise, the second free portion 406b is moveable with respect to the central axis 401 by an angle $\theta_2$. The values for the angle $\theta_2$ can be, for example, ten degrees, forty-five degrees, ninety degrees, one-hundred thirty-five degrees, one-hundred eighty degrees, etc. Desirably, the angle $\theta_2$ corresponds to the geometry of a main branch of a bifurcation in the parent vessel. For example, the angle $\theta_2$ can be substantially equal to an angle at which a main branch extends from a central axis of the bifurcation of the parent vessel. By allowing the value for $\theta_2$ to range between zero and one-hundred eighty degrees, the second free portion 406b can be positioned at or near to a branch of the bifurcation having any given geometry.

The dual guidewire lumen catheter 400 is also similar to the dual guidewire lumen catheter 100 (FIG. 1D) in that the first distal end 410a and the first distal aperture 412a can define a first beveled surface 414a. Additionally, the second distal end 410b and the second distal aperture 412b can define a second beveled surface 414b. As discussed above, each beveled surface is configured to aid in placement of the first guidewire and the second guidewire in a branch of a bifurcation. The beveled surfaces also reduce or eliminate sharp edges at either distal end, thereby reducing the risk of injury. The first beveled surface 414a of the first distal end 410a and the second beveled surface 414b of the second distal end 410b can be beveled at the same angle, or alternatively, each can be beveled at a different angle.

Like the dual guidewire lumen catheter 100 shown in FIG. 3, the dual guidewire lumen catheter 400 can include a balloon (not shown in FIGS. 4A and 4B) coupled thereto such that the first distal end 410a and the second distal end 410b extend beyond the balloon. The extent to which the first distal end 410a and second distal end 410b extend beyond the balloon depends on the geometry of the target bifurcation. For example, as shown, the length L2 of the first free portion 406a is greater than the length L3 of the second free portion 406b such that the first distal end 410a extends beyond the second distal end 410b. In addition, like the dual guidewire lumen catheter 100 shown in FIG. 3, the dual guidewire lumen catheter 400 can further include a stent (not shown) coupled to the balloon. Dilation of the balloon causes the stent to be deployed in the target vessel.

Figure 5A:
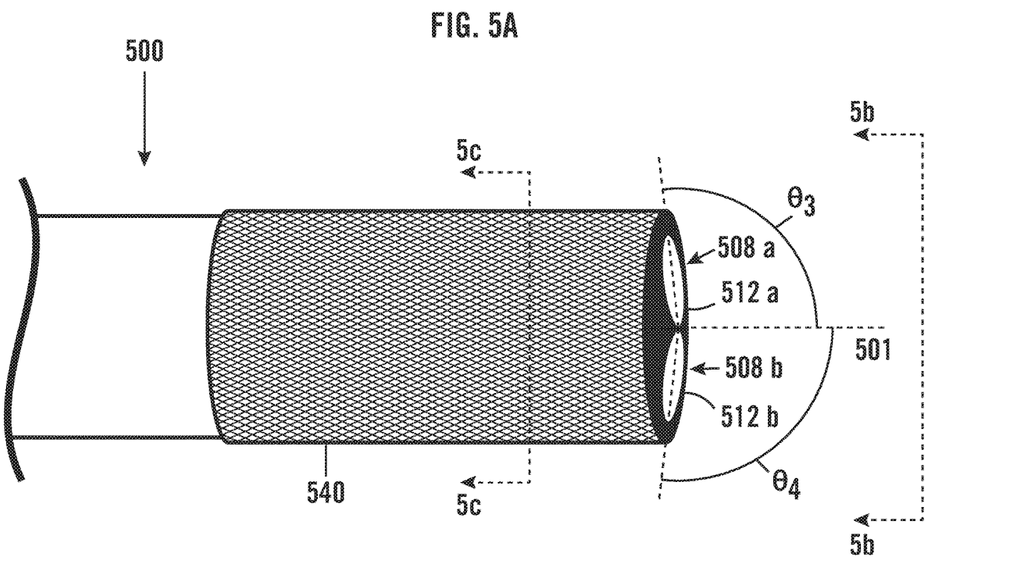
FIG. 5A is a perspective view of a portion of a dual guidewire lumen catheter according to some aspects of the present disclosure.
Figure 5B:
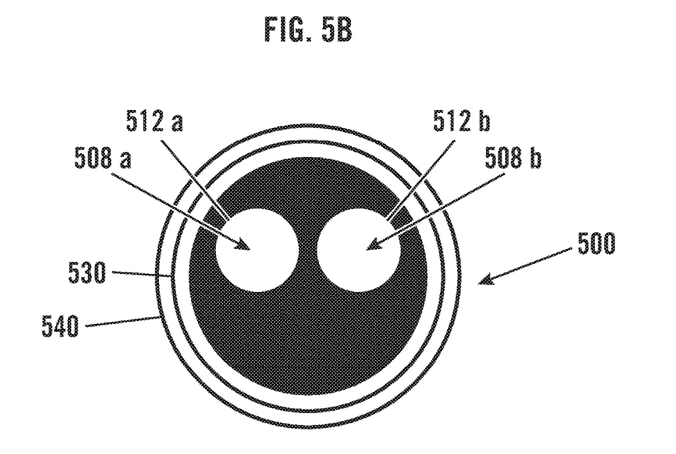
FIG. 5B is an end-on view of the dual guidewire lumen catheter of FIG. 5A according to some aspects of the present disclosure.

Referring generally to FIGS. 5A and 5B, a dual guidewire lumen catheter 500 is shown. The dual guidewire lumen catheter 500 is configured to be deployed in a blood vessel having a bifurcation.

The dual guidewire lumen catheter 500 is similar to the dual guidewire lumen catheter 100 (FIGS. 1A-1D) and the dual guidewire lumen catheter 400 (FIGS. 4A and 4B) in that the dual guidewire lumen catheter 500 includes a first guidewire lumen 508a and a second guidewire lumen 508b. The dual guidewire lumen catheter 500 differs from the dual guidewire lumen catheter 100 and the dual guidewire lumen catheter 400 in that it does not include a pair of elongated members. Rather, as shown, the dual guidewire lumen catheter 500 has a generally cylindrical profile with a first guidewire lumen 508a and a second guidewire lumen 508b extending there through.

The first guidewire lumen 508a is configured to receive a first guidewire (not shown) and the second guidewire lumen 508b is configured to receive a second guidewire (not shown). As best shown in FIG. 5B, the first guidewire lumen 508a has a first distal aperture 512a and the second guidewire lumen 508b has a second distal aperture 512b.

In some aspects, the first distal aperture 512a of the first guidewire lumen 508a can define a plane that is angled with respect to a central axis 501 of the dual guidewire lumen catheter 500. As best shown in FIG. 5A, the plane defined by the first distal aperture 512a is angled with respect to the central axis 501 by an angle $\theta_3$. The values of the angle $\theta_3$ can be, for example, forty-five degrees, ninety degrees, one hundred thirty-five degrees, one hundred fifty degrees, etc. By allowing the value for the angle $\theta_3$ to vary as described, the first distal aperture 512a can be positioned at or near a branch of a bifurcation having any given geometry. In addition, in some aspects, the angle $\theta_3$ can further aid in preventing the first guidewire from becoming intertwined with the second guidewire.

Likewise, in some aspects, the second distal aperture 512b of the second guideiwre lumen 508b can define a plane that is angled with respect to the central axis 501 of the dual guidewire lumen catheter 500. As best shown in FIG. 5A, the plane defined by the second distal aperture 512b is angled with respect to the central axis 501 by an angle $\theta_4$. The values of the angle $\theta_4$ can be, for example, forty-five degrees, ninety degrees, one-hundred thirty-five degrees, one hundred fifty degrees, etc. By allowing the value for the angle $\theta_4$ to vary as described, the second distal aperture 512b can be positioned at or near a branch of a bifurcation having any given geometry. In addition, in some aspects, the angle $\theta_4$ can further aid in preventing the second guidewire from becoming intertwined with the first guidewire. While the angle $\theta_3$ and the angle $\theta_4$ are shown as having substantially equal values in FIG. 5A, it is contemplated that the angles $\theta_3$, $\theta_4$ can have different values.

In some aspects, the dual guidewire lumen catheter 500 is formed such that the first distal aperture 512a defines a plane angled by the angle $\theta_3$ and the second distal aperture defines a plane angled by the angle $\theta_4$, as shown in FIG. 5A. Alternatively, in other aspects, the dual lumen catheter can be formed such that the angle $\theta_3$ and the angle $\theta_4$ are both substantially equal to ninety degrees. In such aspects, the first distal aperture 112a and the second distal aperture 112b can be cut or shaved such that each defines a plane that is angled with respect to the central axis 501. Advantageously, this configuration allows the dual guidewire lumen catheter to be modified given the needs of the present application, and more specifically, the geometry of the blood vessel having the bifurcation.

Referring to FIG. 5A, in some aspects, the dual guidewire lumen catheter 500 also includes a stent 540 coupled to a balloon 530 (FIGS. 5B and 5C) such that the first distal aperture 512a of the first guidewire lumen 508a and the second distal aperture 512b of the second guidewire lumen 508b extend beyond the balloon 530. Dilation of the balloon 530 causes the stent 540 to be deployed. The stent 540 is appropriately sized such that it can be deployed within the target vessel. Deployment of the stent 540 can be optimized, if necessary, with existing intravascular imaging techniques.

Figure 5C:
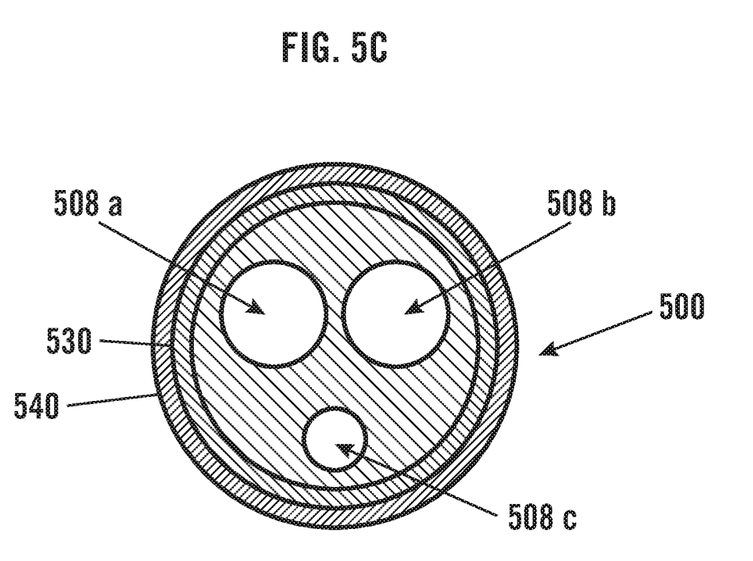
FIG. 5C is a cross-sectional view of the dual guidewire lumen catheter of FIG. 5A according to some aspects of the present disclosure.

As best shown in FIG. 5C, in some aspects, the dual guidewire lumen catheter 500 includes a third lumen 508c. The third lumen 508c differs from the first guidewire lumen 508a and the second guidewire lumen 508c in that it does not fully extend through the dual guidewire lumen catheter 500. Rather, the third lumen 508c only extends from a proximal portion of the dual guidewire lumen catheter up until a portion to which the balloon 530 and stent 540 are coupled. The third lumen 508c is configured to allow inflation of the balloon 530 in order to deploy the stent 540. Similarly, in such aspects of the present disclosure in which the dual guidewire lumen catheter 100 includes a balloon (FIGS. 2 and 3) and the dual guidewire lumen catheter 400 includes a balloon (not shown in FIGS. 4A and 4B), each dual guidewire lumen catheter 100, 400 can also include a third lumen that is the same or similar to the third lumen 508c.

While the first guidewire lumen 508a and second guidewire lumen 508b are shown as having substantially equal diameters, the first guidewire lumen 508a can have a diameter that is greater than the diameter of the second guidewire lumen 508b, and conversely, the second guidewire lumen 508b can have a diameter that is greater than the diameter of the first guidewire lumen 508a. Generally, the diameter of the first guidewire lumen 508a and the diameter of the second guidewire lumen 508b are greater than the diameter of the first guidewire and the second guidewire, respectively, in order to facilitate movement of the first guidewire within the first guidewire lumen 508a and movement of the second guidewire within the second guidewire lumen 508b.

Figure 6A:
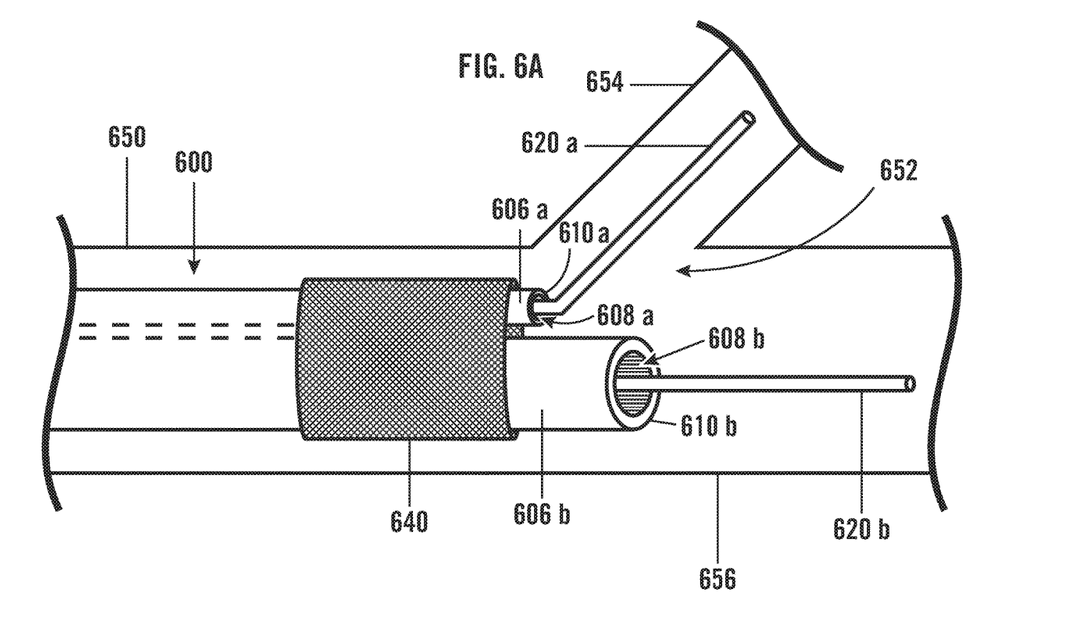
FIG. 6A is a perspective view of a dual guidewire lumen catheter disposed at a bifurcation of a parent vessel according to some aspects of the present disclosure.
Figure 6B:
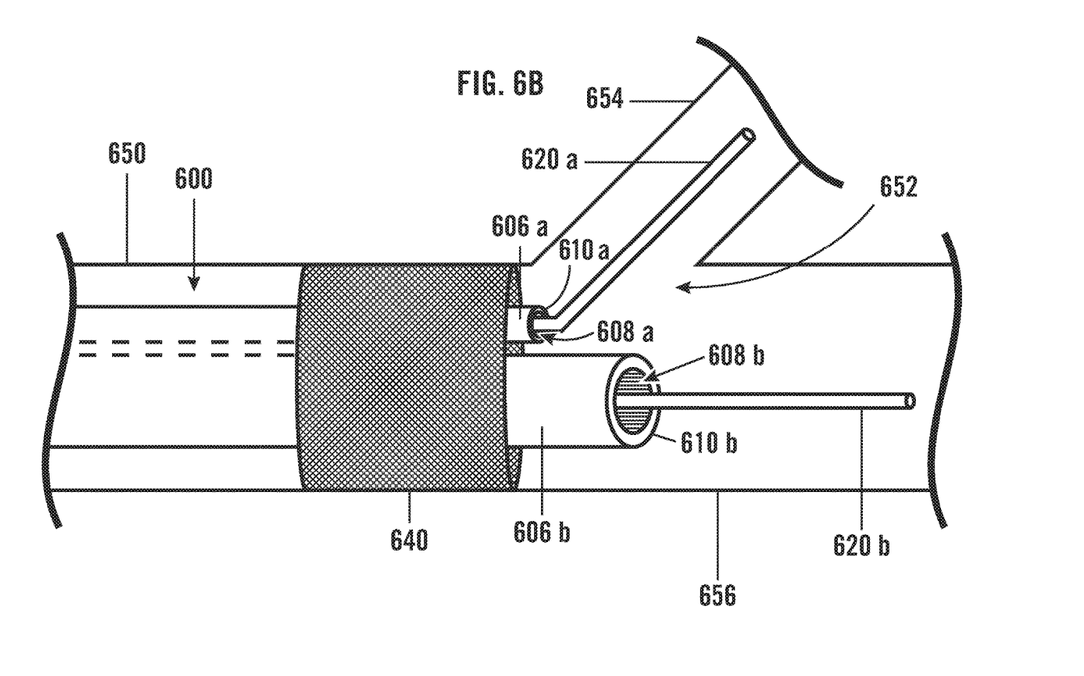
FIG. 6B is a perspective view of a stent of the dual guidewire lumen catheter of FIG. 5A in a deployed position according to some aspects of the present disclosure.

Referring generally to FIGS. 6A-6E, a method of using a dual lumen (e.g., multi-lumen) catheter 600 of the present disclosure is shown according to some aspects. In FIGS. 6A and 6B, the dual guidewire lumen catheter 600 is deployed in a parent vessel 650. The dual guidewire lumen catheter 600 is similar to the dual guidewire lumen catheter 400 shown in FIGS. 4A and 4B in that the dual guidewire lumen catheter 600 includes a first elongated member 602a having a first free portion 606a and a second elongated member 602b having a second free portion 606b. The first elongated member 602a has a first lumen 608a configured to receive a first guidewire 620a there through and the second elongated member 602b has a second lumen 608b configured to receive a second guidewire 620b there through. The dual guidewire lumen catheter 600 differs from the dual guidewire lumen catheter 400 of FIGS. 4A and 4B in that the second free portion 606b has a length that is greater than the length of the first free portion 606a. As such, the second distal end 610b of the second free portion 606b extends beyond the first distal end 610a of the first free portion 606a. Additionally, the dual guidewire lumen catheter 600 differs from the dual guidewire lumen catheter 400 shown in FIGS. 4A and 4B in that the dual guidewire lumen catheter 600 includes a stent 640 coupled over a balloon (not shown).

As depicted, the parent vessel 650 includes a bifurcation 652. Beyond the bifurcation 652, the parent vessel 650 branches off into a side branch 654 and a main branch 656. As shown, the side branch 654 has a diameter that is smaller than the diameter of the parent vessel 650, and the main branch 656 has a diameter that is substantially equal to the diameter of the parent vessel 650. However, the dimensions of the parent vessel 650, the side branch 654, and the main branch 656 can vary depending on the geometries of the target parent vessel with the bifurcation. Thus, the first elongated member 602a has a diameter that generally corresponds to the diameter of the side branch 654 in that the diameter of the first elongated member 602a is smaller than the diameter of the side branch 654. Similarly, the second elongated member 602b has a diameter that generally corresponds to the diameter of the main branch 656 in that the diameter of the second elongated member 602b is smaller than the diameter of the main branch 656.

In treating a target lesion occurring at a bifurcation, such as the bifurcation 652 shown in FIGS. 6A-6E, dilation of the parent vessel 650 and/or the main branch 656 can result in plaque shift to the adjacent side branch 654. Loss of blood flow to the myocardium supplied by either the side branch 654 or main branch 656 can result in myocardial infarction or persistent ischemia.

To aid in preventing plaque shift, the first guidewire 620a is advanced through a first proximal end (not shown) of the first elongated member 602a and the second guidewire 620b is advanced through a second proximal end (not shown) of the second elongated member 602b. The first guidewire 620a is advanced through the first elongated member 602a until the first guidewire 620a extends through the first distal end 610a and into the parent vessel 650. The first guidewire 620a is then advanced past the stenosis of the side branch 654 of the bifurcation 652. The second guidewire 620b can then be advanced through the second distal end 610b of the second elongated member 602b and into the parent vessel 650. The dual guidewire lumen catheter 600 is then advanced into the parent vessel 650 along the first guidewire 620a and the second guidewire 620b. After advancing the dual guidewire lumen catheter 600, the second guidewire 620b is then advanced into the main branch 656 of the bifurcation 652. The dual guidewire lumen catheter is then advanced along the first guidewire 620a and second guidewire 620b up to the bifurcation 652, as depicted in FIG. 6A. In this configuration, the first guidewire 620a and second guidewire 620b prevent the dual guidewire lumen catheter 600 from being inadvertently advanced into the side branch 654 or the main branch 656. Further, the dual guidewire lumen catheter 600 prevents the first guidewire 620a from being intertwined with the second guidewire 620b.

Subsequent to the dual guidewire lumen catheter 600 being advanced up to the bifurcation 652, the procedure can be varied. In some aspects, the dual guidewire lumen catheter 600 includes the balloon (not shown in FIG. 6A), but does not include the stent 640 as shown in FIG. 6A. The balloon can be used in order to predilate the lesion as necessary prior to stent deployment. In such aspects, the dual guidewire lumen catheter 600 is retreated from the parent vessel 650 along the first guidewire 620*a* and the second guidewire 620*b* subsequent to predilation of the parent vessel 650. At this point, a second dual guidewire lumen catheter including a stent coupled to a balloon can be advanced up to the bifurcation using the same method as discussed above. The second dual guidewire lumen catheter is otherwise the same as the dual guidewire lumen catheter 600.

Referring to FIG. 6B, subsequent to the predilation of the parent vessel 650 as described above, or alternatively, subsequent to advancing the dual guidewire lumen catheter 500 up to the bifurcation 652 if the predilation step is not required, the stent 640 is deployed in the parent vessel 650. To deploy the stent 640, the balloon (not shown) is appropriately dilated. The stent 640 is appropriately sized such that it conforms to the dimensions of the parent vessel 650. Stent deployment can be optimized, if necessary, with existing intravascular imaging techniques.

Figure 6C:
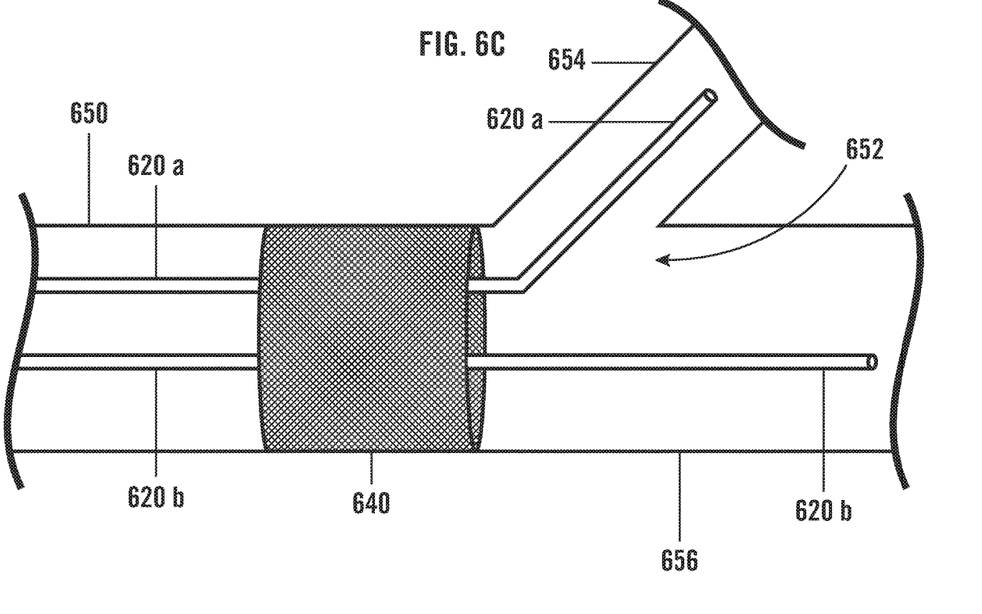
FIG. 6C is a perspective view of the stent in the deployed position of FIG. 5B with the dual guidewire lumen catheter removed according to some aspects of the present disclosure.

Referring to FIG. 6C, after deploying the stent 640 in the parent vessel 650, the dual guidewire lumen catheter 600 is retreated from the parent vessel 650 along the first guidewire 620*a* and the second guidewire 620*b*. As shown, the first guidewire 620*a* remains in the side branch 654 and the second guidewire 620*b* remains in the main branch 656 subsequent to the dual guidewire lumen catheter 600 being retreated. As discussed above, initially positioning the first guidewire 620*a* and the second guidewire 620*b* in their respective branches using the dual guidewire lumen catheter 600 prevents the guidewires 620*a* and 620*b* from becoming intertwined and facilitates placement of subsequent devices.

In some aspects, subsequent to retreating the dual guidewire lumen catheter 600, the side branch 654 and/or the main branch 656 can be predilated prior to deploying a stent in either branch. In such aspects, a first predilation catheter is advanced along the first guidewire 620*a* such that a distal end of the first predilation catheter is disposed at or near the side branch 654. Likewise, a second predilation catheter is advanced along the second guidewire 620*b* such that a distal end of the second predilation catheter is disposed at or near the main branch 656. The first predilation catheter includes a first balloon and the second predilation catheter includes a second balloon. The first balloon and the second balloon can then be simultaneously dilated in order to optimally dilate the side branch 654 and/or the main branch 656. The first predilation catheter and the second dilation catheter are then retreated along the first guidewire 620*a* and the second guidewire 620*b*, respectively.

Figure 6D:
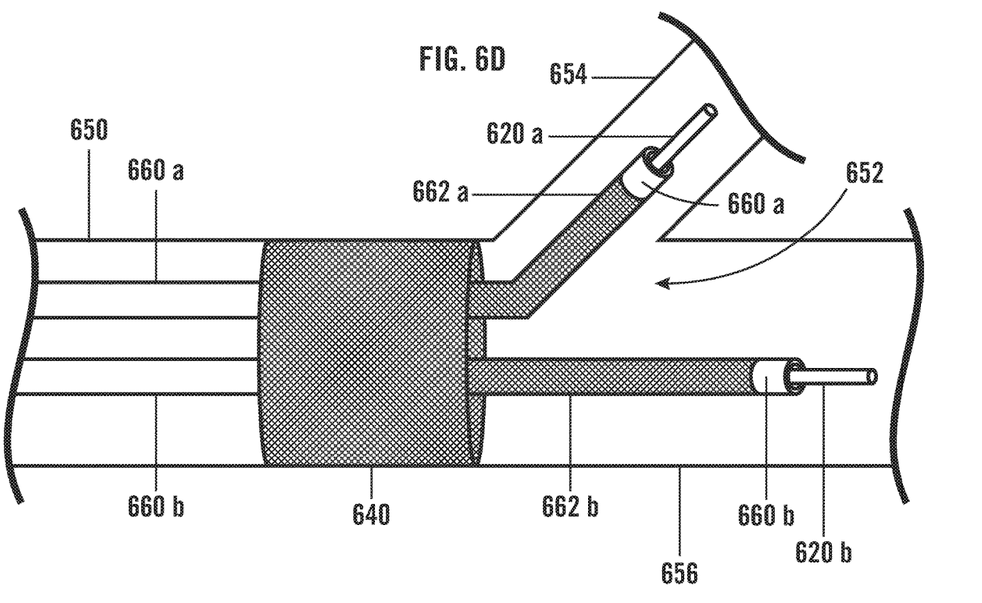
FIG. 6D is a perspective view of positioning of a side branch stent and a main branch stent relative to the deployed stent as shown in FIG. 5C according to some aspects of the present disclosure.

Referring to FIG. 6D, subsequent to predilating the side branch 654 and/or the main branch 656, or alternatively, subsequent to retreating the dual guidewire lumen catheter 600 if the predilation step is not required, a first stent deployment catheter 660*a* is advanced along the first guidewire 620*a* and a second stent deployment catheter 660*b* is advanced along the second guidewire 620*b*. The first stent deployment catheter 660*a* includes a side branch stent 662*a* coupled to a balloon (not shown). The side branch stent 662*a* is appropriately sized such that it conforms to the dimensions of the side branch 654. The second stent deployment catheter 660*b* includes a main branch stent 662*b* coupled to a balloon (not shown). The main branch stent 662*b* is appropriately sized such that it conforms to the dimensions of the main branch 656. As depicted, the side branch stent 662*a* and the main branch stent 662*b* are positioned in the side branch 654 and the main branch 656 such that there is some overlap with the stent 640 in the parent vessel 650.

Figure 6E:
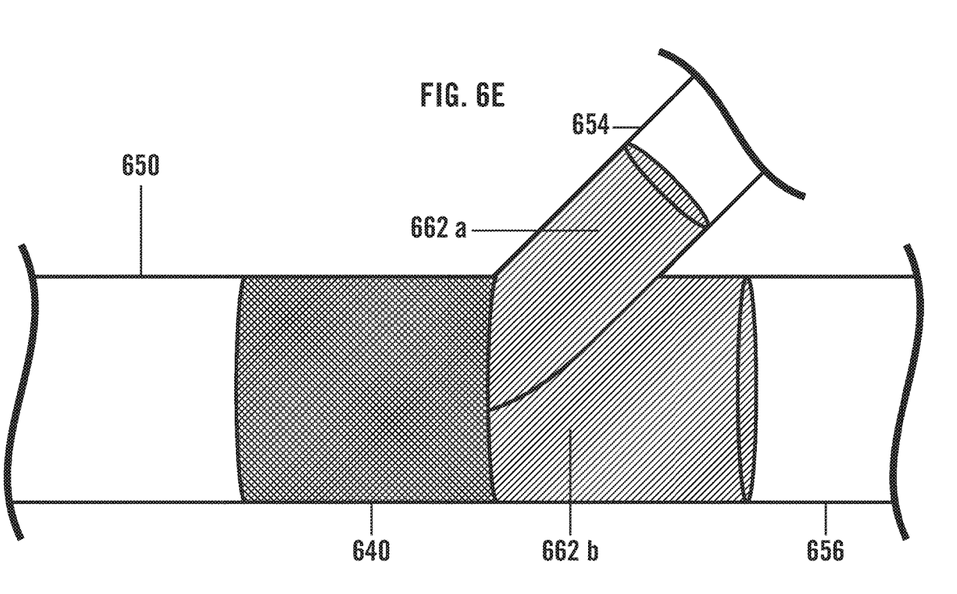
FIG. 6E is a perspective view of the side branch stent and the main branch stent of FIG. 5D each in a deployed position according to some aspects of the present disclosure.

The side branch stent 662*a* and the main branch stent 662*b* are then deployed using a "kissing balloon" technique. As shown in FIG. 6E, deploying the side branch stent 662*a* in the side branch 654 and the main branch stent 662*b* in the main branch 656 results in raising the bifurcation. Stent deployment can be optimized, if necessary, with existing intravascular imaging techniques.

While aspects of the present disclosure have been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present invention may combine any number of features from any of the embodiments described herein.

What is claimed:

1. A multi-lumen catheter system, comprising:
a dual guidewire lumen catheter including a first elongated member and a second elongated member,
the first elongated member having a first integral portion and a first free portion, the first elongated member extending a length from a proximal end of the dual guidewire lumen catheter to a distal end of the dual guidewire lumen catheter, the first integral portion and the first free portion including a first lumen extending through the first integral portion and the first free portion, the first lumen being configured to route a first guidewire through the dual guidewire lumen catheter and through a bifurcation of a vessel, the first free portion having a first distal end and a first aperture configured to receive the first guidewire,
the second elongated member extending a length of the first integral portion and including a second distal end of a second integral portion and a second lumen extending through the second elongated member, the second lumen being configured to route a second guidewire through the dual guidewire lumen catheter and through the bifurcation of the vessel, the second distal end having a second aperture configured to receive the second guidewire, the second elongated member being integral with the first integral portion of the first elongated member and the first free portion being moveable with respect to a central axis of the catheter;
a balloon coupled to the dual guidewire lumen catheter such that the first distal end of the first free portion and the second distal end of the second integral portion extend beyond the balloon, the balloon being configured to dilate the vessel; and
a stent surrounding the balloon and being configured to be deployed within the vessel at the bifurcation based on dilation of the balloon.

2. The system of claim 1, wherein the first aperture and the first distal end of the first free portion of the first elongated member define a first beveled surface configured to aid in placement of the first guidewire in a side branch of the bifurcation of the vessel and the second aperture and the second distal end of the second elongated member define a second beveled surface configured to aid in placement of the second guidewire in a main branch of the bifurcation of the vessel.

3. The system of claim 1, wherein the first elongated member includes a diameter corresponding to a dimension of a side branch of the bifurcation of the vessel and the second elongated member includes a diameter corresponding to a dimension of a main branch of the bifurcation of the vessel.

4. The system of claim 1, wherein at the bifurcation of the vessel comprises within the vessel and proximal to a side branch of the vessel.

5. The system of claim 1, wherein the balloon is continuous from the distal end of the balloon to a proximal end of the balloon.

6. The system of claim 1, wherein
the balloon is a central perfusion balloon that defines a channel when inflated to allow blood to flow past the central perfusion balloon.

\* \* \* \* \*